(12) United States Patent
McConnell et al.

(10) Patent No.: US 9,863,966 B2
(45) Date of Patent: Jan. 9, 2018

(54) IMMUNOASSAYS FOR MEPERIDINE AND METABOLITES

(71) Applicant: Randox Laboratories Limited, Crumlin (GB)

(72) Inventors: Ivan McConnell, Crumlin (GB); Elouard Benchikh, Crumlin (GB); Philip Lowry, Crumlin (GB); Peter Fitzgerald, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 586 days.

(21) Appl. No.: 14/048,325

(22) Filed: Oct. 8, 2013

(65) Prior Publication Data

US 2014/0099651 A1  Apr. 10, 2014

(30) Foreign Application Priority Data

Oct. 8, 2012 (GB) .................................... 1217938

(51) Int. Cl.
*G01N 33/94* (2006.01)
*C07K 16/44* (2006.01)
*A61K 47/48* (2006.01)

(52) U.S. Cl.
CPC ......... *G01N 33/94* (2013.01); *A61K 47/4833* (2013.01); *A61K 47/48284* (2013.01); *C07K 16/44* (2013.01); *C07K 2317/33* (2013.01)

(58) Field of Classification Search
CPC .......... A61K 47/48284; A61K 47/4833; C07K 16/44; C07K 2317/33; G01N 33/94
See application file for complete search history.

(56) References Cited

U.S. PATENT DOCUMENTS 3,120,541 A * 2/1964 Rolf Denss .......... C07D 211/64
544/130
7,115,718 B2 * 10/2006 McConnell ...... A61K 47/48284
435/188

OTHER PUBLICATIONS

Ratcliffe et al., "Development of a monoclonal antibody for the detection of meperidine and its metabolite normeperidine," Clinical Chemistry and Laboratory Medicine, (May 2011) vol. 49, No. Suppl. 1, pp. S797, Abstract 1182.*
A print-out "Anti-meperidine/normeperidine antibody from Randox Biosciences," Catalog No. PAS9860, retrieved from http://www.biocompare.com/9776-Antibodies/1051009-Sheep-AntiMEPERIDINE-NORMEPERIDINE-Polyclonal-Antibody-Unconjugated/ on Jun. 7, 2016 (3 pages total).*
Ratcliffe et al., "Development of two monoclonal antibodies for the broad detection of barbiturates and for the detection of meperidine and the metabolite normeperidine," 2011 SOFT-TIAFT, Sep. 25-30, 2011, P222 (3 pages total).*
Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*
Pravetoni et al., "Structurally distinct nicotine immunogens elicit antibodies with non-overlapping specificities," Biochem. Pharmacol., Feb. 15, 2012; vol. 83, No. 4, pp. 543-550, Published online Nov. 15, 2011.*
Englebienne, "Immune and Receptor Assays in Theory and Practice," CRC Press, 2000, p. 308.*
Shim et al., "Monoclonal Antibody-Based Enzyme-Linked Immunosorbent Assays for the Organophosphorus Insecticide O-Ethyl O-4-Nitrophenyl Phenylphosphonothioate (EPN)," J. Agric. Food Chem., 2010, vol. 58, No. 9, pp. 5241-5247.*
Freeman et al., "Radioimmunoassay for normeperidine: studies on the N-dealkylation of meperidine and anileridine," J. Pharm. Exp. Ther., 1977, vol. 203, No. 1, pp. 203-212.*
Baselt, R.C. (ed). 2008. Meperidine in Disposition of Toxic Drugs and Chemicals in Man. 8th edition, Biomedical Publications, Foster City, California, pp. 911-914.
DePriest, A. et al. 2010. Urine drug testing of chronic pain patients. III. Normetabolites as biomarkers of synthetic opioid use. J Anal Toxicol, 34, 444-449.
Foley et al. 1983. Central nervous system excitatory effects of meperidine in cancer patients. Ann Neurol, 13: 180-185.
Jerrard, D.A. 1990. "Designer drugs"—a current perspective. J Emerg Med, 8(6):733-41.
Jiang Z. 1992. Iatrogenic addiction of pethidine: clinical feature and experience of detoxification. Zhonghua Shen Jing Jing Shen Ke Za Zhi, 25(2).85-7, 126.
Koczmara, C. et al. 2005. Meperidine (Demerol) safety issues. ISMP Canada Safety Bulletin spring 2005.
Latta, K.S. et al. 2002. Meperidine: A critical review. Am J Ther, 9, 53-68.
Marcantonio , E.R et al. 1994. The relationship of post-operative delirium with psychoactive medications. JAMA, 272, 1518-1522.
Murphree, H.B. 1962 Clinical pharmacology of potent analgesics. Clin Pharmcol Ther, 3:473-450.
Sweetman, S.C. (ed). 2011. Martindale: The Complete Drug Reference, 37th edition. Pharmaceutical press, London, UK. ISBN 9780853699330.
Umans, J.G. & Inturrisi C.E. 1982. Antiociceptive activity and toxicity of meperidine and normeperidine in mice. J Pharmacol Exp Ther, 223:203-206.
Wallot, H. & Lambert, J. 1982. Drug addiction among Quebec physicians. Can Med Assoc J, 126(8):927-30.

* cited by examiner

*Primary Examiner* — Galina Yakovleva
(74) *Attorney, Agent, or Firm* — Hodgson Russ LLP

(57) ABSTRACT

The invention provides novel haptens and immunogens for the preparation of novel monoclonal antibodies, which detect the synthetic opioid meperidine and its active metabolite normeperidine. These antibodies enable methods and kits, which are useful in an immunoassay for therapeutic drug monitoring (TDM) and in extending the window of detection for cases of abuse and drug-facilitated sexual assault (DFSA).

1 Claim, 3 Drawing Sheets

Hapten-1

N-Carboxyethyl normeperidine

A.

B.

IMMUNOASSAYS FOR MEPERIDINE AND METABOLITES

CROSS-REFERENCE TO RELATED APPLICATIONS

This application relies on and claims the benefit of UK patent application 1217938.8, filed 8 Oct. 2012, the entire disclosure of which is incorporated herein by reference.

BACKGROUND OF THE INVENTION

Meperidine is a synthetic opioid analog that is frequently used for acute pain management. It is derived from phenylpiperidine and is active at both the mu- and kappa-opioid receptors. Meperidine is also commonly known as pethidine or by its brand name Demerol. Compared to morphine, it has a shorter duration but faster onset of action and is around 7-10 times less potent (Latta et al., 2002). It is administered in the form of meperidine hydrochloride, which is supplied for oral administration as either tablets (50 or 100 mg) or as syrup (10 mg/ml). A solution of the drug (25-100 mg/ml) is also available for parenteral injection and can be given epidurally, intraperitoneally, or intrathecally (Baselt, 2008).

Meperidine hydrochloride is readily absorbed from the gastrointestinal tract and is rapidly and extensively distributed throughout the tissues (Moffat et al., 2003). The most clinically significant metabolic pathway is through N-demethylation to form normeperidine, the only active metabolite (Latta et al., 2002). FIG. 1 shows the structure of meperidine and normeperidine. Meperidine undergoes first-pass metabolism, meaning that only around 50% reaches systematic circulation. About 7% of meperidine will be excreted unchanged in urine and around 17% will be eliminated in the form of normeperidine (Baselt, 2008). Approximately 70% of the administered dose will be excreted in urine within 24 hours (Moffat et al., 2003). Absorption of the drug varies when administered as an intramuscular injection, with peak plasma concentrations occurring 1-2 hours after administration. The plasma elimination half-lives of meperidine and normeperidine are 3-4 hours and 15-20 hours, respectively (Demerol Prescribing Information datasheet, Sanofi-Aventis). Normeperidine is only half as effective an analgesic as its parent compound. However, it has up to 3 times the neurotoxic potential, having significant adverse effects on the central nervous system (CNS). It is also more active as a convulsant and has an extended half-life (14-48 hours, as opposed to 3-6 hours for meperidine) (Latta et al., 2002). It is excreted renally and thus the half life is prolonged in patients with renal dysfunction. Normeperidine is rarely detected in plasma following a single administration (Baselt, 2008). However, it can accumulate in plasma following chronic administration, particularly following renal failure (Moffat et al., 2003) and may be detected at concentrations greater than the parent drug (Baselt, 2008). The ratio of normeperidine to meperidine has been suggested as an important indicator of possible CNS excitation side effects, with a ratio greater than one representing a higher risk (Kaiko et al., 1983). Both meperidine and normeperidine have been detected in cerebrospinal fluid (Sweetman, 2011). Meperidine/normeperidine side effects can be manifested as a wide range of symptoms with varying degrees of severity including irritability, agitation, tremors, tachycardia, muscle twitches, hypertension, disorientation, and grand mal seizures. A daily dose of meperidine as low as 260 mg has been reported to cause grand mal seizures, while doses as low as 46 mg per day have been reported as causing muscle twitches or tremors (Latta et al., 2002). Meperidine has also been linked with increased risk of delirium in elderly patients (Marcantonio et al., 1994) and possesses complex pharmacodynamics not in common with other first-line opioids, including inhibition of the re-uptake of the neurotransmitter serotonin, which can lead to the potentially fatal serotonin syndrome (Latta et al., 2002). In addition, these side-effects are not reversible with traditional opioid antagonists such as naxolone, which by antagonizing the depressant effects may even enhance the convulsant activity of meperidine/normeperidine (Umans & Inturrisi, 1982).

The ease of availability and short duration of action has made meperidine a favourite drug of abuse amongst medical professionals (Murphree, 1962; Wallot & Lambert 1982). Although iatrogenic addiction following long-term medication of narcotic analgesics has been noticed, it has rarely been documented (Jiang, 1992). Addiction to meperidine has similar characteristics to heroin addiction, and physical withdrawal can be managed using methadone or clonidine (Jiang, 1992). There have also been reports of the alteration and modification of controlled substances, including meperidine, to produce "designer drugs" that have previously been able to temporarily elude controlled substance regulations (Jerrard, 1990). Both meperidine and its active metabolite normeperidine are target analytes on the society of forensic toxicologists (SOFT) list for the detection limits of common drugs used in drug facilitated sexual assault (DFSA). In the United States, meperidine including its isomers, esters, salts, and salts of isomers, has been placed on schedule II of the Controlled Substances Act (DEA) and in the UK (as pethidine) under class A.

Due to concerns surrounding its toxic side-effects, many health care organisations are either restricting its use or phasing it out altogether, replacing it with less toxic opioid analgesics. However, meperidine may still be beneficial for short-term pain management, treatment of post-operative shivering, and the prevention and treatment of drug-induced or blood product-induced rigors (Koczmara et al., 2005). When it is still administered, it would be important to accurately monitor build-up of the parent and especially the active metabolite in patients. Currently available antibodies/immunoassays for meperidine have low cross reactivity with normeperidine and thus, if used for therapeutic drug monitoring (TDM) purposes, may grossly underestimate levels of this toxic metabolite (Table 1). A liquid chromatography based study found a 98.7% increase in detection of positive specimens when both meperidine and normeperidine were measured compared to meperidine on its own (DePriest et al., 2010). The unique properties, including the high sensitivity of the monoclonal antibody described herein, which detects both the parent drug and its metabolite in approximately a one to one ratio, would be beneficial for use in immunoassays, for TDM purposes, and in extending the window of detection for cases of abuse and DFSA.

TABLE 1

Specificity of a selection of available meperidine antibodies/immunoassays*

| Supplier | Product | Meperidine Sensitivity ($IC_{50}$) | Normeperidine specificity (Relative to meperidine 100%) |
|---|---|---|---|
| Neogen | Meperidine ready-to-use kit | Not disclosed | 2.3% |

TABLE 1-continued

Specificity of a selection of available meperidine antibodies/immunoassays*

| Supplier | Product | Meperidine Sensitivity ($IC_{50}$) | Normeperidine specificity (Relative to meperidine 100%) |
|---|---|---|---|
| Immunalysis | direct ELISA kit | ≈40 ng/ml | 7.0% |
| International Diagnostic Systems | Polyclonal Ab | Not disclosed | 12.7% |

*data taken from manufacturers instructions for use

SUMMARY OF THE INVENTION

The invention describes novel haptens and immunogens for the preparation of novel antibodies, including monoclonal antibodies, which are useful in detecting the synthetic opioid meperidine and its active metabolite, normeperidine. These antibodies enable methods and kits, which each can be used in the therapeutic drug monitoring (TDM) of patients requiring meperidine administration and for detection in cases of meperidine abuse and drug-facilitated sexual assault (DFSA).

According to a first aspect of the present invention, there is provided an immunogen having the general structure (I):

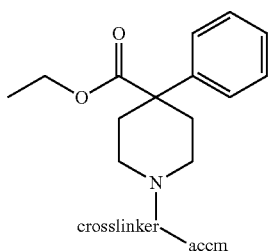

(I)

wherein, accm is an antigenicity conferring carrier material selected from a protein, a protein fragment, a synthetic polypeptide, and a semi-synthetic polypeptide.

Optionally, the accm is selected from bovine serum albumin (BSA), egg ovalbumin, bovine gamma globulin, bovine thyroglubulin (BTG), and keyhole limpet haemocyanin (KLH). Further optionally, the accm is selected from bovine serum albumin (BSA) and bovine thyroglubulin (BTG). Still further optionally, the accm is bovine thyroglubulin (BTG).

Alternatively, the accm comprises synthetic poly(amino acids) having a sufficient number of available amino groups, such as lysine. Further alternatively the accm is selected from a synthetic or natural polymeric material bearing reactive functional groups. Still further alternatively, the accm is selected from carbohydrates, yeasts, and polysaccharides.

Optionally, the crosslinker has the general structure (II):

(II)

wherein, n=0 or 1;

X, when present, is selected from a carbonyl or thionyl group;

Y is a $C_{1-10}$, substituted or unsubstituted, straight or branched chain, alkylene or arylene, moiety; optionally a $C_{2-6}$, substituted or unsubstituted, straight or branched chain, alkylene or arylene, moiety; and Z, before connection to the antigenicity conferring carrier material (accm), is selected from a carboxyl, dithiopyridyl, maleimidyl, amino, thiol, ester, thioester, and an aldehyde moiety.

For illustrative purposes, the nitrogen (N) atom of the general structure (I) of the immunogen is included in the general structure (II) of the crosslinker. However, it will be appreciated that the nitrogen (N) atom of the general structure (I) of the immunogen and the nitrogen (N) atom of the general structure (II) of the crosslinker are the same nitrogen (N) atom.

For illustrative purposes, the accm of the general structure (I) of the immunogen is included in the general structure (II) of the crosslinker. However, it will be appreciated that the accm of the general structure (I) of the immunogen and the accm of the general structure (II) of the crosslinker are the same accm.

Optionally, the crosslinker has the general structure (III) —(X)n-Y—Z—; wherein n=0 or 1; X, when present, is selected from a carbonyl or thionyl group; Y is a $C_{1-10}$, substituted or unsubstituted, straight or branched chain, alkylene or arylene, moiety; optionally a $C_{2-6}$, substituted or unsubstituted, straight or branched chain, alkylene or arylene, moiety; and Z, before connection to the antigenicity conferring carrier material (accm), is selected from a carboxyl, dithiopyridyl, maleimidyl, amino, thiol, ester, thioester, and an aldehyde moiety.

Optionally, the crosslinker is attached to the nitrogen (N) atom of the general structure (I) of the immunogen. Further optionally, X of the crosslinker, when present, is attached to the nitrogen (N) atom of the general structure (I) of the immunogen. Alternatively, Y of the crosslinker, when X is not present, is attached to the nitrogen (N) atom of the general structure (I) of the immunogen.

Optionally, the crosslinker is attached to the accm of the general structure (I) of the immunogen. Further optionally, Z of the crosslinker is attached to the accm of the general structure (I) of the immunogen.

Optionally, the crosslinker has the general structure (III) —(X)n-Y—Z—; wherein n=0; Y is a $C_2$, unsubstituted, straight chain, alkylene moiety; and Z, before connection to the antigenicity conferring carrier material (accm), is a carboxyl moiety.

Further optionally, the immunogen has the general structure (I):

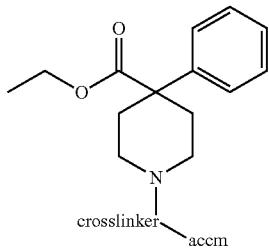
(I)

wherein, accm is bovine serum albumin (BSA); and the crosslinker has the general structure (III) —(X)n-Y—Z—; wherein n=0; Y is a $C_2$, unsubstituted, straight chain, alkylene moiety; and Z, before connection to the antigenicity conferring carrier material (accm), is a carboxyl moiety.

Alternatively, the immunogen has the general structure (I):

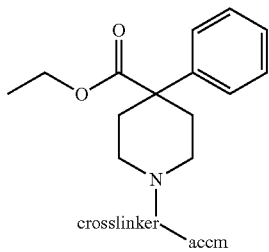
(I)

wherein, accm is bovine thyroglobulin (BTG); and the crosslinker has the general structure (III) —(X)n-Y—Z—; wherein n=0; Y is a $C_2$, unsubstituted, straight chain, alkylene moiety; and Z, before connection to the antigenicity conferring carrier material (accm), is a carboxyl moiety.

Optionally, in substitute for the accm, the immunogen can have a labelling agent. In such a case, the present invention provides a detecting agent (or conjugate).

Optionally, the conjugate comprises a labelling agent selected from an enzyme, a luminescent substance, a radioactive substance, and a mixture thereof. Further optionally, the labelling agent is an enzyme, preferably a peroxidase, most preferably horseradish peroxidase (HRP). Alternatively, or additionally, the luminescent substance may be a bioluminescent, chemiluminescent, or fluorescent material.

According to a second aspect of the present invention, there is provided an antibody derivable from an immunogen according to the first aspect of the invention.

Optionally, the antibody is derived from an immunogen according to the first aspect of the invention.

Optionally, the antibody is a polyclonal antibody. Alternatively, the antibody is a monoclonal antibody.

Optionally, the antibody has 100% cross-reactivity to meperidine. Further optionally or additionally, the antibody has at least 50% cross-reactivity to normeperidine. Further optionally or additionally, the antibody has 80-120% cross-reactivity with normeperidine.

Optionally, the antibody exhibits sensitivity to both meperidine and normeperidine, with $IC_{50}$ values of about 0.5 ng/ml.

Optionally, the antibody is capable of binding, optionally selectively binding, to an epitope of meperidine and normeperidine.

A further aspect of the present invention relates to a method of detecting meperidine and/or normeperidine in a sample, the method comprising the steps of contacting the sample with at least one antibody according to the second aspect of the present invention; and determining qualitative or quantitative presence or absence of meperidine and/or normeperidine bound to the at least one antibody.

Optionally, the method comprises the additional step of contacting the sample with a detecting agent (or conjugate) according to the present invention.

According to a further aspect of the present invention, there is provided an immunoassay for detecting meperidine and/or normeperidine in a sample, the immunoassay comprising at least one antibody according to the invention.

Optionally, the immunoassay further comprises at least one detecting agent (or conjugate) according to the present invention.

The invention also relates to a kit for detecting meperidine and/or normeperidine, the kit comprising: at least one antibody according to the invention; at least one detecting agent (or conjugate) according to the present invention; and instruction for use.

DETAILED DESCRIPTION OF THE INVENTION

Figure 1:
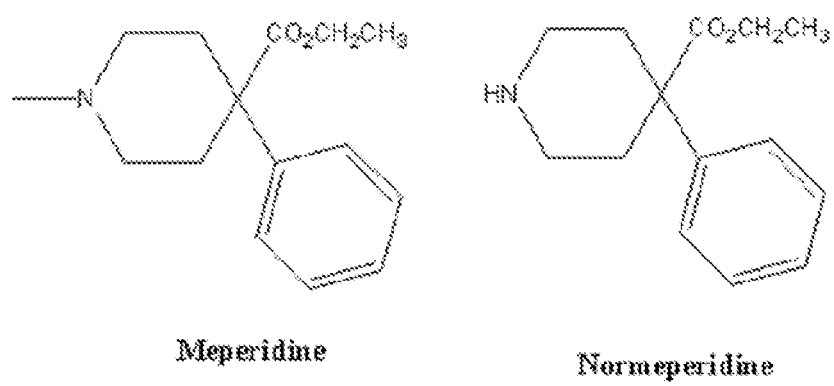
FIG. 1 depicts the structure of meperidine and its active metabolite normeperidine.

The invention provides an immunogen of the structure:

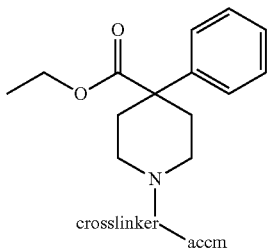

The crosslinker of the immunogen described in the invention is preferably of the structure:

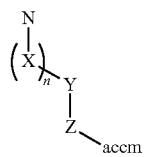

in which X is carbonyl or thionyl and n=0 or 1; Y is a $C_{1-10}$, preferably a $C_{2-6}$, substituted or unsubstituted straight chain alkylene moiety, or an arylene moiety; Z, before connection to the antigenicity conferring carrier material (accm), is carboxy, dithiopyridyl, maleimide, amino, thiol, ester, thioester, or an aldehyde moiety.

The accm is an antigenicity conferring carrier material and is any material that makes all or part of the meperidine/normeperidine moiety susceptible to antibody recognition and binding. For example the accm can be a protein, a protein fragment, a synthetic polypeptide, or a semi-synthetic polypeptide. The accm is preferably bovine thyroglubulin (BTG).

Another aspect of the invention relates to antibodies raised from one or more of the previously described immunogens. The ability of the antibodies to recognise the parent meperidine molecule as well as the active metabolite normeperidine enables uses such as a TDM test for patients administered meperidine, for example, for short term pain management, treatment of post-operative shivering, and/or the prevention and treatment of drug-induced or blood product-induced rigors. It also allows an increased window of detection and reduction in the number of missed positive tests in cases of substance abuse as well as DFSA due to the longer half-life of normeperidine.

The antibodies are characterized by having 100% cross-reactivity to meperidine and at least 50% cross-reactivity to normeperidine. Most preferably they have cross-reactivity with normeperidine of 80-120%. Additionally, the antibodies of the current invention are characterised by their high sensitivity to both meperidine and normeperdine with $IC_{50}$ values of about 0.5 ng/ml. The $IC_{50}$ is a common measure of antibody sensitivity for immunoassays. It is also recognized that, for immunoassays that utilize a competitive format, the exact $IC_{50}$ value varies slightly depending on the nature of the conjugate used to compete with the analyte in the sample.

The antibodies are preferably a monoclonal antibody but the skilled person will understand that any type of immunoglobulin molecule or fragment thereof can be used, for example polyclonal antibodies, Fab fragments, scFv fragments, and any other antigen binding fragments, all of which fall within the scope of the current invention.

A further aspect of the current invention is a hybridoma cell line NM4.3F5.C10.B7.B2.B2.C4 as deposited under the under the Budapest Treaty with the European Collection of Cell Cultures (ECACC) under deposit number 12090501. Antibodies and fragments thereof produced from this hybridoma are also covered by the current invention. Antibodies which bind to the same epitope as those produced from this hybridoma are also included in the scope of the invention.

The invention also provides a method for detecting or determining one or more of meperidine and normeperidine in a sample, the method comprising contacting the sample with one or more detecting agents and one or more antibodies of the invention; detecting or determining the quantity of the one or more detecting agents; and deducing from calibrators, the presence of or amount of one or more of meperidine or normeperidine in the sample. For the purposes of the invention, the patient sample to be used for in vitro analysis can be hair or a peripheral biological fluid, but is preferably whole blood, serum, plasma, or urine.

As mentioned herein, the term "detecting" means qualitatively analyzing for the presence or absence of a substance while "determining" means quantitatively analyzing for the amount of a substance. The detecting agent is a small molecule, generally of similar structure to a molecule to be detected conjugated to a labelling agent, that is able to bind to one of the antibodies of the invention. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. A further aspect of the current invention is a kit for detecting or determining one or more of meperidine and normeperidine, the kit comprising one or more antibodies as described above and one or more conjugates.

GENERAL METHODS, EXAMPLES AND RESULTS

Preparation of Haptens, Immunogens, and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins, and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent, such as an enzyme (for example, horseradish peroxidase), a substance having fluorescent properties, or a radioactive label for the preparation of detecting agents (conjugates) for use in the immunoassays. The fluorescent substance may be, for example, a monovalent residue of fluorescein or a derivative thereof. Immunogen formation for the invention described herein involves conventional conjugation chemistry. In order to confirm that adequate conjugation of the hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 μl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig, or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification. However, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule, such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate, such as a polystyrene solid support or a ceramic chip. The antibodies can be polyclonal or monoclonal using standard techniques. The signal emitted in the immunoassay is proportionate to the amount of detecting agent bound to the antibodies, which in turn is inversely proportionate to the analyte concentration. The signal can be detected or quantified by comparison with a calibrator.

Materials and Methods

Pre-immunisation blood samples were collected from 16-month-old female Suffolk sheep. On Day 0, each sheep was immunized intramuscularly with normeperidine conjugated via an amino group to a carrier protein, bovine thyroglobulin (BTG). Subsequent boosts were administered intramuscularly to each sheep every 30 days. Freund's complete adjuvant was used for primary immunizations and Freund's incomplete adjuvant was used for all subsequent injections. Routine bleeds were taken between boosts to monitor the antibody titre and sensitivity, using normeperidine conjugated to Horseradish peroxidase in a competitive ELISA testing cross reactivity to meperidine and normeperidine.

After polyclonal serums of good quality were collected, the monoclonal protocols were given precedence. Once the antibody titres were assessed as meeting the required performance criteria, two final peri-nodal boosts were administered spaced 30 days apart. Four days following the final peri-nodal boost, lymph nodes were harvested from the Left Axillary, Right Axillary, Left Prescapular, and Right Prescapular regions. The lymph nodes were first perfused with media, and then dissected using scissors and forceps to gently tease apart each piece of lymph node. The scissors and forceps were then used to scrape the remaining lymphocytes from the tissue into the cell suspension. All cells, except those required for the lymph node cell assay (LNCA), were frozen using 90% FBS 10% DMSO at a density of $2\times10^8$. The LNCA incubated 24 ($1\times10^6$) lymphocytes from each node location at 5% $CO_2$, 37° C. for 7 days before collecting supernatant from each well for testing as above (polyclonal bleed assessment). The cells from these LNCA plates were then discarded.

The LNCA were used to determine whether nodes met standard fusion criteria. Fusion of lymphocytes with a heteromyleoma cell-line was carried out at a ratio of approximately 2:1 by adding 0.5 ml PEG 1500 slowly over 1 minute. The PEG was then diluted using serum-free DMEM and the cells were allowed to stand for 5 minutes before being plated using 140 ml of 20% DMEM P/S with ×1HAT into 7×96 well plates (200 µl per well). On Day 7, the media was replenished on each fusion plate with 20% DMEM P/S with ×1HAT and, on Day 14, 180 µl/well of supernatant was removed and screened using ELISA. The wells were replenished this time with 20% DMEM P/S with ×1 HT. The hybridoma culture supernatants were initially screened using the method above (polyclonal bleed assessment). Positive hybridomas were cloned to produce stable monoclonal hybridomas using 1% methylcellulose at 37° C., 5% $CO_2$ chosen either from positive fusion wells or from established, but unstable cell lines. One cell line, NM4.3F5.C10.B7.B2.B2.C4, was identified as meeting specifications and was cloned three times, with good supporting assay results. Positive cell lines were then confirmed as being monoclonal using limit dilution. Single colonies were identified after 7 days and screened for antibody production. Once confirmed as being stable and 100% clonal, the resulting cell-lines were expanded at 37° C., 5% $CO_2$ for 4 weeks. After 4 weeks, the supernatants were pooled and purified via Protein A purification.

Antibodies were then evaluated by competitive immunoassay. They were first immobilized on a biochip platform (9 mm×9 mm), which was the vessel for the immunoreactions. The semi-automated bench top analyser Evidence Investigator was used (EV3602, Randox Laboratories Ltd., Crumlin, UK, patents-EP98307706, EP98307732, EP0902394, EP1227311, EP1434995 and EP1354623). The assay principle is based on competition for binding sites of the monoclonal antibody between free antigen and labelled conjugate. Sample and reagents are added to the biochip and incubated under controlled conditions. Following addition of substrate, a light signal is generated which is then detected using digital imaging technology. The system incorporates dedicated software to automatically process, report, and archive the data generated.

Examples

Figure 2:
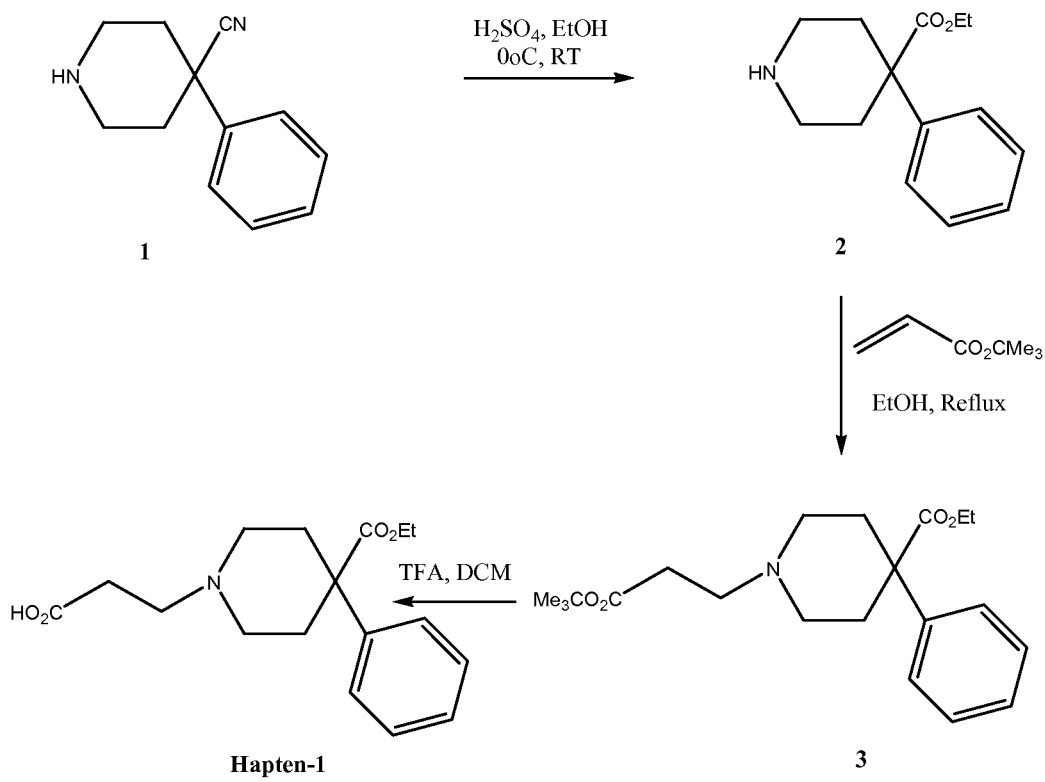
FIG. 2 depicts chemical reactions for the synthesis of Hapten-1.

Numbers in Bold Refer to Structures in FIG. 2

Example-1: Preparation of Normeperidine 2

To a cooled solution 0° C. of 4-phenyl-4-cyanopiperidine 1 (10 g, 0.044 mol) in Ethanol (30 ml) was added drop-wise a solution of concentrated $H_2SO_4$ (15 ml) and the mixture was heated at reflux for 48 hrs. The mixture was then poured into crushed ice and the ethanol was removed under vacuum. The aqueous solution was made alkaline by saturated $Na_2CO_3$ solution and extracted with ethyl acetate (3×100 ml). The combined organic layers were washed by water, brine, dried over $Na_2SO_4$ and concentrated to dryness to afford 5.28 g of thick light brown oil, which later turned to a soft wax of normeperidine 2.

Example-2: Preparation of N-(Carboterbutoxyethane)Normeperidine 3

To a cooled solution 0° C. of normeperidine 2 (2.0 g, 0.0086 mol) in ethanol (50 ml) under nitrogen was added solid Sodium Ethoxide (0.7 g, 0.0103 mol) and t-butyl acrylate (2.8 ml, 0.0168 mol) and the mixture was then stirred at room temperature overnight. The ethanol was removed under vacuum and the residue obtained was portioned between ethyl acetate and water. The organic layer was washed by water, brine, dried over $Na_2SO_4$ and concentrated to dryness. The crude product was purified by flash chromatography on silica gel using ethyl acetate/hexane (50/50) to afford N-(Carboterbutoxyethane) normeperidine 3 (2.4 g) as a thick yellow oil.

Example-3: Preparation of N-(Carboxyethyl)Normeperidine [Hapten-1 (FIG. 2)]

To a solution of N-(Carboterbutoxyethane) normeperidine 3 (2.4 g, 0.0066 mol) in dichloromethane (10 ml) was added trifluoroacetic acid (TFA) (10 ml) and the mixture was stirred at room temperature overnight. The mixture was concentrated to dryness, and the crude product obtained was purified by chromatography on silica gel using 20% MeOH/CHCl$_3$ to afford N-(Carboxyethyl) Normeperidine (Hapten-1) (2.1 g) as a viscous clear oil.

Example 4: Conjugation of Hapten-1 to BSA (Immunogen-I)

To a solution of N-(Carboxyethyl) Normeperidine (Hapten-1) (54.96 mg, 0.18 mmol) in DMF (1.0 ml) was added N,N-dicyclohexylcarbodiimide (DCC) (40.85 mg, 0.198 mmol) and N-hydroxysuccinimide (22.78 mg, 0.198 mmol) and the mixture was stirred at room temperature overnight. The dicyclohexylurea formed was removed by filtration and the solution was added drop-wise to a solution of BSA (150 mg, 2.3 µmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried. MALDI results showed 11.3 molecules of hapten-1 had been conjugated to one molecule of BSA.

Example 5: Conjugation of Hapten-1 to BTG (Immunogen-II)

To a solution of N-(Carboxyethyl) Normeperidine (Hapten-1) (61.99 mg, 0.203 mmol) in DMF (1.0 ml) was added N,N-dicyclohexylcarbodiimide (DCC) (46.01 mg, 0.223 mmol) and N-hydroxysuccinimide (25.66 mg, 0.223 mmol) and the mixture was stirred at room temperature overnight. The dicyclohexylurea formed was removed by filtration and the solution was added drop wise to a solution of BTG (150 mg, 2.25 µmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried.

Example 6: Conjugation of Hapten-1 to HRP

EDC hydrochloride (10 mg) was dissolved in water (0.5 ml) and immediately added to a solution of N-(Carboxyethyl) Normeperidine (Hapten-1) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-columns (Pharmacia) in series, pre-equilibrated with PBS at pH 7.2. The hapten-HRP conjugate was then dialysed overnight against 10 L of PBS at pH 7.2 at 4° C.

Results

Figure 3:
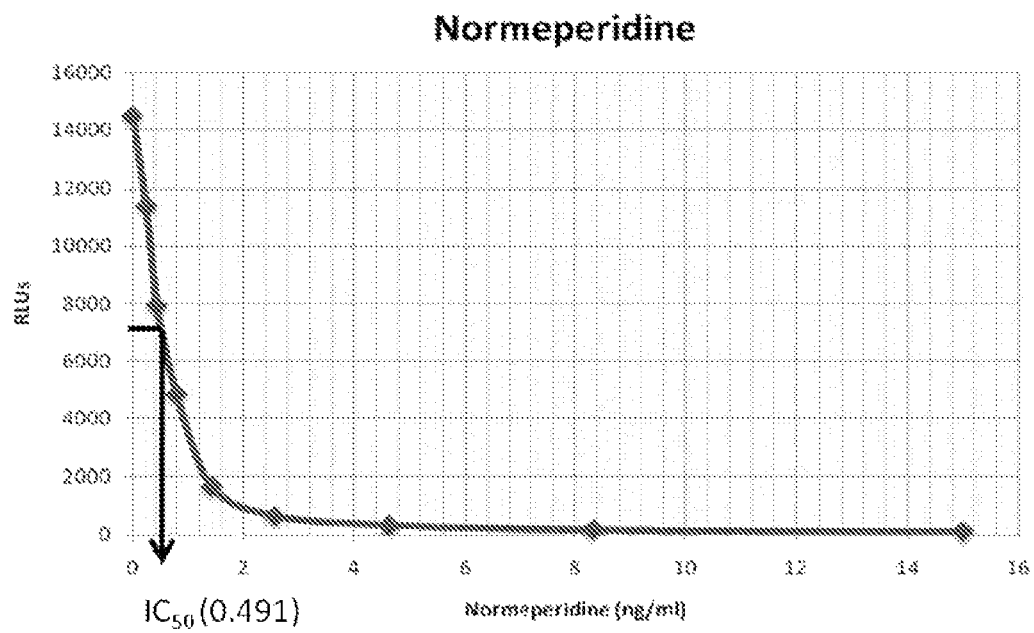
FIG. 3A depicts a calibration curve for normeperidine immunoassays.
FIG. 3B depicts a calibration curve for meperidine immunoassays. The calibration range for detection of both analytes was 0-15 ng/ml.
Figure 3:
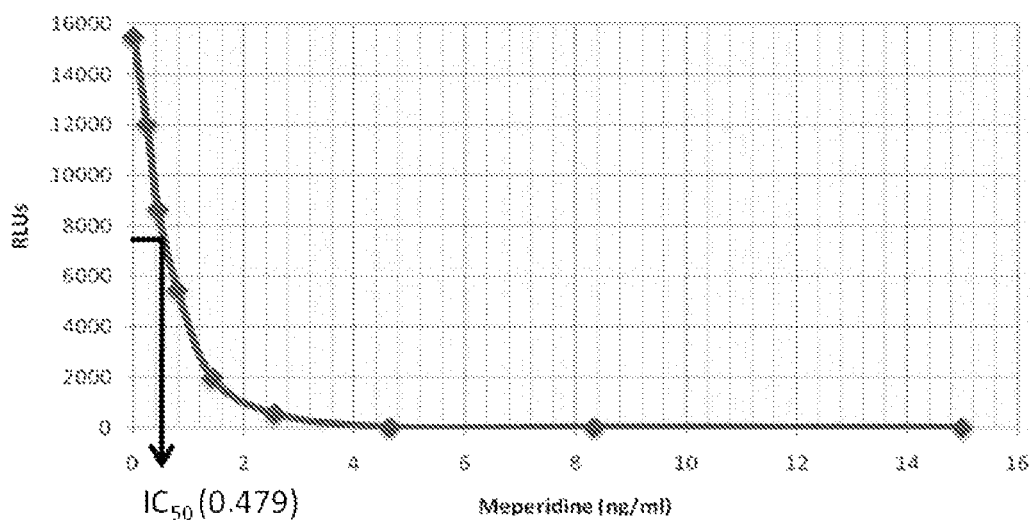

Calibration curves were generated using the Biochip based immunoassay (FIGS. 3A and 3B). The IC$_{50}$ was calculated from the graphs by taking 50% of the signal from the zero calibrator and reading the corresponding value on the x-axis, equivalent to the concentration of unlabelled ligand which reduces specific binding of labelled ligand by 50%. Specificity was also tested against a range of related analytes (Table 2).

TABLE 2

Specificity expressed as percentage cross reactivity (% CR)

| Analyte | % Cross Reactivity* |
| --- | --- |
| Normeperidine | 100 |
| Meperidine | 102.5 |
| Buprenorphine HCl | <1 |
| Butorphanol Tartrate | <1 |
| Codeine | <1 |
| Ethyl-Glucuronide | <1 |
| Fentanyl | <1 |
| 7-NH-Flunitrazepam | <1 |
| Hydrocodone | <1 |
| Hydromorphone | <1 |
| Levorphanol | <1 |
| Morphine Sulfate Salt | <1 |
| Meprobamate | <1 |
| Methadone | <1 |
| Nalbuphine | <1 |
| Norketamine | <1 |
| Oxycodone | <1 |
| Oxymorphone | <1 |
| Pentazocine | <1 |
| Urochloralic Acid | <1 |
| Zaleplon | <1 |
| Zolpidem | <1 |
| Zopiclone | <1 |

*% CR = [IC50 (analyte)/IC50 (cross-reactant)] × 100; Typical intra-assay precision: Co-efficient of variance <11% for different concentration levels.

REFERENCES

Baselt, R. C. (ed). 2008. Meperidine in *Disposition of Toxic Drugs and Chemicals in Man.* 8$^{th}$ edition, Biomedical Publications, Foster City, Calif., pp 911-914.

DePriest, A. et al. 2010. Urine drug testing of chronic pain patients. III. Normetabolites as biomarkers of synthetic opioid use. *J Anal Toxicol,* 34, 444-449.

Jerrard, D. A. 1990. "Designer drugs"—a current perspective. *J Emerg Med,* 8(6):733-41.

Jiang Z. 1992. Iatrogenic addiction of pethidine: clinical feature and experience of detoxification. *Zhonghua Shen Jing Jing Shen Ke Za Zhi,* 25(2):85-7, 126.

Kaiko et al. 1983. Central nervous system excitatory effects of meperidine in cancer patients. *Ann Neurol,* 13: 180-185.

Koczmara, C. et al. 2005. Meperidine (Demerol) safety issues. *ISMP Canada Safety Bulletin spring* 2005.

Latta, K. S. et al. 2002. Meperidine: A critical review. *Am J Ther,* 9, 53-68.

Marcantonio, E. R et al. 1994. The relationship of postoperative delirium with psychoactive medications. *JAMA,* 272, 1518-1522.

Moffat, A. C et al. (eds). 2003. Clarkes analysis of Drugs and Poisons, 3$^{rd}$ edition. Pharmaceutical press, London, UK. ISBN 0853694737.

Murphree, N. B. 1962 Clinical pharmacology of potent analgesics. *Clin Pharmcol Ther,* 3:473-450.

Sweetman, S. C. (ed). 2011. Martindale: The Complete Drug Reference, 37$^{th}$ edition. Pharmaceutical press, London, UK. ISBN 9780853699330.

Umans, J. G. & Inturrisi C. E. 1982. Antiociceptive activity and toxicity of meperidine and normeperidine in mice. *J Pharmacol Exp Ther,* 223:203-206.

Wallot, H. & Lambert, J. 1982. Drug addiction among Quebec physicians. *Can Med Assoc J,* 126(8):927-30.

The invention claimed is:

1. A competitive immunoassay method of detecting or determining meperidine and/or normeperidine in a sample, the method comprising:

contacting the sample with the monoclonal antibody produced by the hybridoma cell line NM4.3F5.C10.B7.B2.B2.C4 deposited with the European Collection of Cell Cultures (ECACC) under deposit reference number 12090501, and with a detecting agent, wherein the detecting agent is N-(carboxyethyl) normeperidine conjugated through its carboxyl group to horseradish peroxidase; and determining the presence and/or amount of meperidine and/or normeperidine in the sample by determining an amount of the detecting agent bound to the monoclonal antibody.

* * * * *